United States Patent [19]

Collins

[11] Patent Number: 4,542,232
[45] Date of Patent: Sep. 17, 1985

[54] PROCESS FOR PREPARING HYDROXYETHYL P-(β HYDROXYETHOXY)BENZOATE

[75] Inventor: Guy R. Collins, Walnut Creek, Calif.

[73] Assignee: The Dow Chemical Company, Midland, Mich.

[21] Appl. No.: 639,761

[22] Filed: Aug. 13, 1984

[51] Int. Cl.$^4$ ............................................. C07C 69/76
[52] U.S. Cl. ................................................... 560/064
[58] Field of Search ........................................... 560/64

[56] References Cited

U.S. PATENT DOCUMENTS 2,802,807  8/1957  Drewitt et al. ..................... 260/45.4
4,261,922  4/1981  Kem ................................ 260/512 R

FOREIGN PATENT DOCUMENTS 2401312  7/1974  Fed. Rep. of Germany .
742793   1/1956  United Kingdom .
573477   9/1977  U.S.S.R. .

OTHER PUBLICATIONS

Ignat'eva, K. E. et al., Zh. Org. Khim., 17 (8), 1728–1730, 1981.
Chem. Abst. 83: 180,287u (1975).

Primary Examiner—Paul J. Killos
Attorney, Agent, or Firm—Michael L. Glenn

[57] ABSTRACT

Excess ethylene carbonate is reacted with p-hydroxybenzoic acid in the presence of a catalytic amount of potassium iodide, potassium bromide, potassium fluoride, cesium iodide or cesium fluoride to make hydroxyethyl p-(hydroxyethoxy)benzoate.

5 Claims, No Drawings

PROCESS FOR PREPARING HYDROXYETHYL P-(β HYDROXYETHOXY)BENZOATE

BACKGROUND OF THE INVENTION

This invention relates to an improved process for preparing hydroxy ethyl p-(βhydroxyethoxy) benzoate. More particularly, this process involves the reaction of p-hydroxybenzoic acid with ethylene carbonate to prepare the title compound.

The reaction of ethylene carbonate with phenol or phenolic compounds in the presence of a cesium or potassium iodide catalyst to prepare hydroxyalkylphenyl ether compounds is disclosed in U.S. Pat. No. 4,261,922. The use of acid or base catalysts for such reactions is described in U.S. Pat. Nos. 2,448,767 and 3,283,030.

British Pat. No. 742,793 discloses that methyl esters of p-hydroxybenzoate can be reacted with cyclic ethylene carbonate to prepare a linear polyester. In the provisional specification of this application, it is noted that cyclic glycol carbonates react readily with free dicarboxylic acids. Diglycol esters are acid of 3:1 or higher. formed at mole ratios of cyclic carbonate to dicarboxylic Japanese Pat. No. 75 16,839 (Chem. Abst. 83:180287u) describes the preparation of hydroxy ethyl p-(βhydroxyethoxy) benzoate by the reaction of p-hydroxybenzoic acid and ethylene oxide. However, this reaction is prone to the formation of poly(ethoxy) groups in the product and is not easily adapted to commercial operations.

The object of the subject process is to provide an improved method of making hydroxy ethyl p-(βhydroxyethoxy) benzoate, hereinafter referred to as "HEHEB". HEHEB is useful as a monomer for fiber-forming polyesters and also as a chain extender for polyurethanes.

SUMMARY OF THE INVENTION

The invention is an improved process for making HEHEB. This process comprises contacting in the liquid phase ethylene carbonate and p-hydroxybenzoic acid in a mole ratio of at least about 2.5 to 1 at a temperature in the range from about 150° C. to about 180° C. in the presence of a catalytic amount of KI, CsI, KBr, KF, or CsF. The HEHEB is then recovered from the reaction medium.

DETAILED DESCRIPTION OF THE INVENTION

It has been surprisingly found that by reacting excess ethylene carbonate with p-hydroxybenzoic acid at specific catalyzed reaction conditions, HEHEB can be prepared in high yield. There is little oligomer or polyester formed in preferred embodiments of this process. Moreover, few poly(ethoxy) groups are introduced. In preferred embodiments of this invention yields of at least about 70 mole percent, more preferably at least about 90 mole percent, HEHEB based on the p-hydroxybenzoic acid reactant are attainable.

The ethylene carbonate and p-hydroxybenzoic acid reactants are both well-known compounds. Both these reactants are available commercially.

The reactants can be brought together in any convenient manner. The use of solvents or diluents inert in the reaction is operable, but not necessary. Advantageously, the reaction is conducted neat.

The mole ratio of ethylene carbonate to p-hydroxybenzoic acid should be at least about 2.5:1, because an excess of ethylene carbonate is necessary to produce the desired HEHEB product in good yield. At a mole ratio of ethylene carbonate ("EC") to p-hydroxybenzoic acid ("PHBA") of 2:1, p-(hydroxyethoxy)benzoic acid is formed almost exclusively. Even larger excesses of ethylene carbonate are preferred. A mole ratio of EC:PHBA of at least about 3:1 is preferred, with at least about 4:1 being more preferred and at least about 4.5:1 being most preferred. Conveniently, the ratio of EC:PHBA does not exceed 10:1.

The reaction temperature is preferably at least about 150° C., more preferably at least about 155° C. and most preferably at least about 160° C., as lower temperatures result in the formation of p-(hydroxyethoxy)benzoic acid reaction. Reaction temperatures above about 180° C. should be avoided because of possible polymerization of the product. Reaction temperatures in the range from about 165° to about 175° C. are especially preferred.

A number of alkaline earth metal halides, e.g., $MgBr_2$ were found to promote formation of poly(ethoxy) moieties. Consequently, these salts are not suitable as catalysts in the subject process. Of those catalysts found suitable, KI, CsI and KBr are preferred, with KI being most preferred.

The loading of the catalyst is not critical so long as the amount present is adequate to promote the desired reaction. In general, the catalyst should be present at a loading of from about 1 to about 10 percent of the total weight of the reactants. Preferably, the catalyst is present in a loading of from about 3 to about 5 percent of the reactants weight.

The reaction medium is advantageously stirred or otherwise agitated to provide good heat and mass transfer. Operable means for agitation will be apparent to the skilled artisan.

The time required for the reaction to reach substantial completion depends on the reaction temperature, the catalyst, the catalyst loading, the concentration of the reactants and other factors. In preferred embodiments of this invention a reaction time of from about 1 hour to about 2 hours is adequate. Less preferred embodiments of this invention may require much longer reaction times. The extent of reaction is conveniently monitored by analysis of the reaction medium or monitoring the carbon dioxide evolved from the medium. The process can be conducted batchwise or continuously.

The HEHEB product can be isolated by conventional techniques, such as extraction followed by distillation. One convenient technique involves washing the reaction medium with water one or more times. Some of these aqueous washes can be saturated with $NH_4OH$ or $NaHCO_3$ followed by acidic neutralizing washes. The washed product layer is separated, dissolved in methylene chloride and washed again with water. The organic layer is separated, treated with a dehydrating agent and the methylene chloride evaporated at reduced pressure. The HEHEB product is isolated in preferred embodiments of this invention in yields of at least about 70 mole percent based on the p-hydroxybenzoic acid, more preferably at least about 90 mole percent.

The following example is presented to illustrate the invention.

EXAMPLE 1

To a reaction vessel equipped with a means for controlling and measuring temperature, a stirrer, gas outlet and condenser was charged 7.95 grams of p-hydroxybenzoic acid (0.0576 mole), 15.21 grams of ethylene carbonate (0.1728 mole) and 0.85 gram KI (0.0051 mole). The reaction mixture was heated to 175° C. Stirring of the reaction mixture was initiated as soon as it became liquid. The gas evolving from the reaction mixture was trapped and analyzed. After about two hours the heating was discontinued. The crude product was a yellow viscous liquid.

After the product mixture had cooled to 70° C., 1 liter of warm (60° C.) water was added and the mixture stirred for 10 minutes. The stirring was stopped and the aqueous layer removed. The organic layer was then washed twice more, first with a saturated aqueous $NaHCO_3$ solution and then water. The product was dissolved in methylene chloride and dried over anhydrous $CaSO_4$. The methylene chloride was then removed by evaporation at reduced pressure. The residue was identified by conventional methods of analysis as hydroxy ethyl p-($\beta$hydroxyethoxy) benzoate.

What is claimed is:

1. A process for preparing hydroxy ethyl p-($\beta$hydroxyethoxy) benzoate comprising the steps of:
    (a) contacting in the liquid phase ethylene carbonate and p-hydroxybenzoic acid in a mole ratio of at least about 2.5:1 at a temperature in the range from about 150° to about 180° C. in the presence of a catalytic amount of KI, CsI, KBr, KF or CsF; and
    (b) recovering hydroxy ethyl p-($\beta$hydroxyethoxy) benzoate from the liquid reaction medium.

2. The process as described in claim 1 wherein the reaction temperature in step (a) is at least 155° C.

3. The process as described in claim 1 wherein the catalyst is KI.

4. The process as described in claim 3 wherein the mole ratio of ethylene carbonate to p-hydroxybenzoic acid is at least about 3:1.

5. The process as described in claim 4 wherein the reaction temperature in step (a) is at least about 160° C.

* * * * *